United States Patent [19]

Plugge et al.

[11] Patent Number: 4,567,898

[45] Date of Patent: Feb. 4, 1986

[54] METHOD AND MEANS FOR IMAGING OBSTRUCTED BLOOD VESSELS

[75] Inventors: Jay S. Plugge, El Dorado Hills, Calif.; Stephen W. Flax, Waukesha, Wis.

[73] Assignee: General Electric Company, Milwaukee, Wis.

[21] Appl. No.: 754,192

[22] Filed: Jul. 10, 1985

Related U.S. Application Data

[63] Continuation of Ser. No. 520,960, Aug. 8, 1983, abandoned.

[51] Int. Cl.[4] .............................................. A61B 10/00
[52] U.S. Cl. ................................................... 128/660
[58] Field of Search ................................. 128/660–663; 73/625–626; 358/112

[56] References Cited

U.S. PATENT DOCUMENTS

| | | | |
|---|---|---|---|
| 4,334,543 | 6/1982 | Fehr | 128/663 |
| 4,442,843 | 4/1984 | Rasor et al. | 128/660 |
| 4,448,200 | 5/1984 | Brooks et al. | 128/660 X |

OTHER PUBLICATIONS

Ophir, J. et al., "Digital Scan Converters in Diagnostic UTS Imaging", Proc. IEEE, vol. 67, #4, Apr. 1979, pp. 654-664.
Barnes, R. W. et al., "An Ultrasound MTI System for Diagnostic Use", IEEE BME Transactions, vol. BME-18, No. 1, Jan. 1971.
Heintzen et al., "Digital C.V. Radiology," article pp. 1-14 and 197 of book *Digital Image Processing in Medicine*, Proc. Hamburg 10-5-1981.
Flax, S. W. et al., "Textural Variations in B-Mode UTS: A Stochastic Model", UTS Imaging 3, 235-257 (1981).
Thurstone, F. L. et al., "Actual Time-Scan Conversion in a Phased Array System", 1977 UTS Symp. Proc., pp. 523-525.
Von Ramm, O. T. et al., "Thaumascan: Design Considerations and Performance Characteristics" Conf: UTS in Med. vol. 1, Seattle, Wash. Oct. 6-10, 1974.
(Author unknown) "A Real-Time UTS Diagnostic System for Simultaneous Image Displays", Electr. Engr. in Japan vol. 16, No. 154, pp. 66-69 (10/79).

*Primary Examiner*—Kyle L. Howell
*Assistant Examiner*—Francis J. Jaworski
*Attorney, Agent, or Firm*—Flehr, Hohbach, Test, Albritton & Herbert

[57] ABSTRACT

Obstructions in a blood vessel are identified and displayed by determining changes in textural patterns based on the ultrasonic waves reflected from the blood vessel. The textural pattern from stationary scatterers, such as found in a clot, remains essentially constant, whereas the texture pattern for moving scatterers such as flowing blood cells is ever changing. By determining and imaging the variations in textural pattern of the reflected ultrasonic waves the identification of obstructions in the vessel is realized.

2 Claims, 7 Drawing Figures

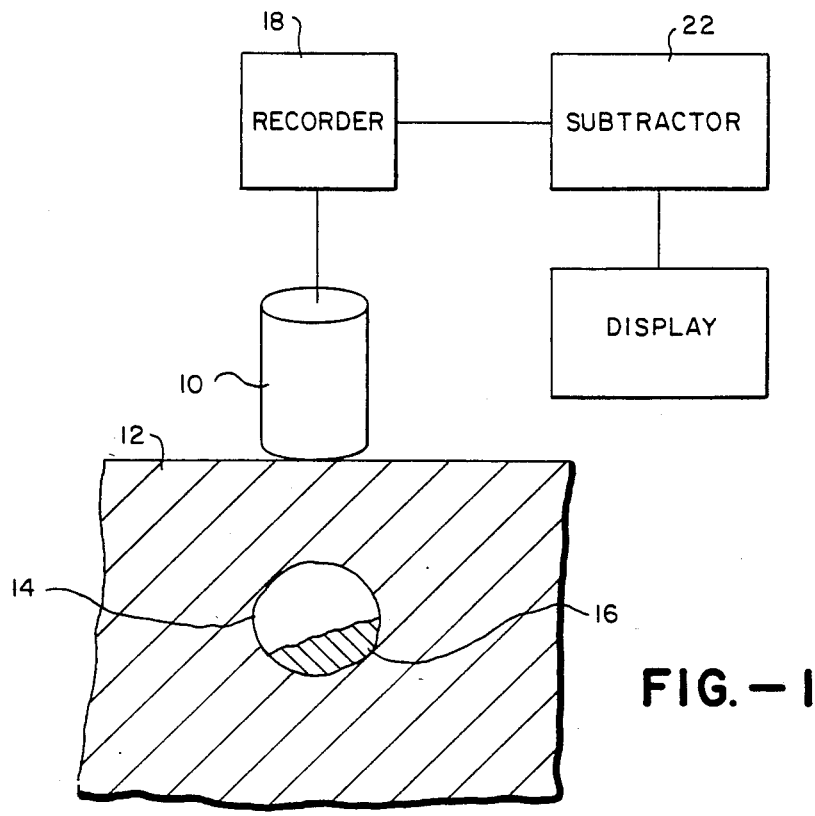
FIG.—1
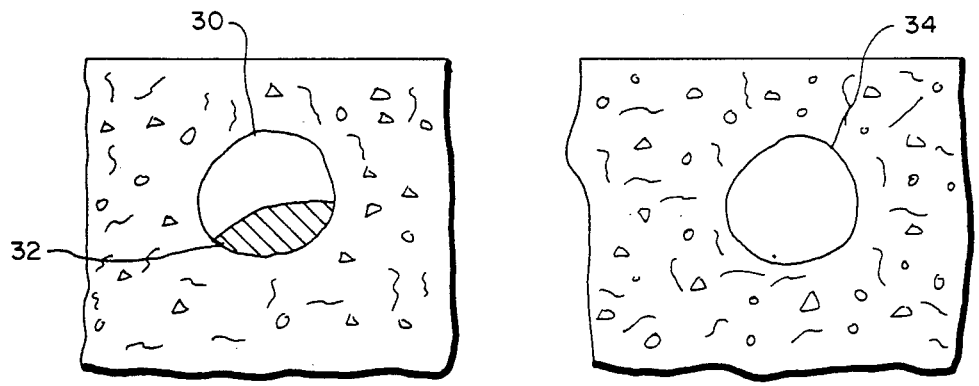
FIG.—2A  FIG.—2B

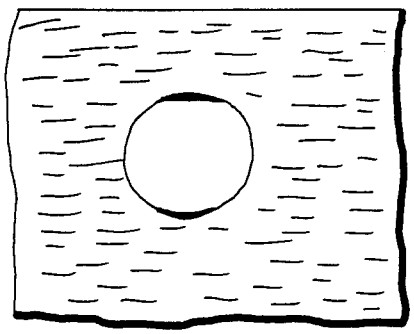
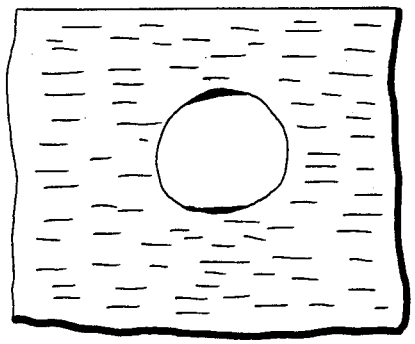
B-SCAN IMAGE SHOWING NO OBSTRUCTION
FIG.—3A  FIG.—3B
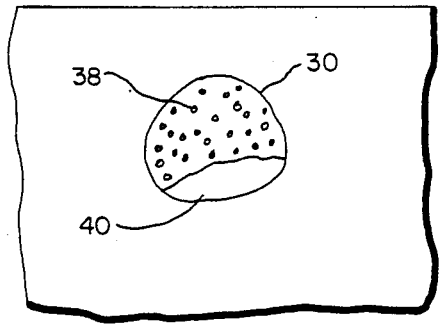
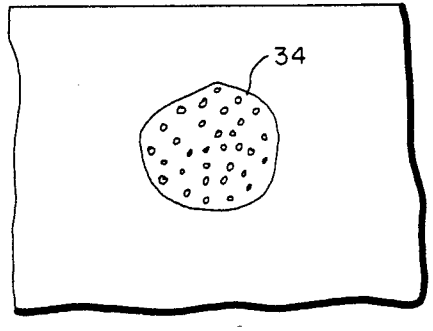
CORRELATION IMAGE SHOWING OBSTRUCTION
FIG.—4A  FIG.—4B

METHOD AND MEANS FOR IMAGING OBSTRUCTED BLOOD VESSELS

This is a continuation of Ser. No. 520,960 filed Aug. 8, 1983 and now abandoned.

This invention relates generally to imaging blood vessels, and more particularly the invention relates to a method and apparatus for imaging cross sections of an obstructed blood vessel and the like.

Attempts at identification of blood clots and lesions in a blood vessel have met with only limited success. For example, ultrasonic body scanners have proved very useful in identifying anatomical features in a human body, but such scanners are unable to distinguish blood from a blood clot since the ultrasonic propagation properties of both are nearly the same.

Flax, Glover, and Pelc, "Textural Variations in B-Mode Ultrasonography: A Stochastic Model", *Ultrasonic Imaging*, 3, pgs 235–257 (1981) note that textural patterns of reflected ultrasonic waves are predictable as a function of distance or depth of stochastic scattering sites. In copending applications Ser. No. 520,959, filed Aug. 5, 1983, and now abandoned for "Ultrasonic Method and Means for Measuring Blood Flow and the Like Using Autocorrelation", Flax describes a method and apparatus for measuring blood flow based on changes in textural patterns of moving scatterers.

The present invention employs the textural patterns of an ultrasonic wave scattering medium to obtain cross sectional images of an obstructed blood vessel. The textural pattern from stationary scatterers, such as a blood clot, remains essentially constant, whereas the textural pattern for moving scatterers such as blood flow is ever changing. Therefore, by determining and imaging variations or changes in textural patterns of reflected ultrasonic waves, the identification of obstructions in a blood vessel can be obtained.

Accordingly, an object of the invention is an improved method of imaging obstructed blood vessels and the like.

Another object of the invention is ultrasonic scanning and imaging apparatus for identifying obstructions in blood vessels.

A feature of the invention is the identity of obstructions based on changes in textural patterns of reflected ultrasonic signals.

The invention and objects and features thereof will be more readily apparent from the following detailed description and appended claims when taken with the drawing, in which:

FIG. 1 is a functional block diagram of apparatus in accordance with the invention for determining and imaging obstructions in blood vessels.

FIG. 2A and FIG. 2B are cross sections of an obstructed blood vessel and an unobstructed blood vessel, respectively.

FIG. 3A and FIG. 3B are images obtained with a conventional ultrasonic body scanner of the vessels of FIGS. 2A and 2B, respectively.

FIG. 4A and FIG. 4B are images of the blood vessels of FIG. 2A and FIG. 2B, respectively, obtained in accordance with the present invention.

Referring now to FIG. 1, a functional block diagram of apparatus for identifying and imaging obstructed blood vessels is illustrated. An ultrasonic transducer 10 is positioned on the surface of tissue 12 directly above a blood vessel 14 which includes an obstructed portion 16. Ultrasonic waves are transmitted through the tissue 12 and blood vessel 14, and reflected ultrasonic signals are received by the transducer 10. Electrical signals generated by the transducer 10 in response to the reflected ultrasonic signals are recorded by recorder 18. Using the conventional electronic components of a B scanner, images of the tissue 12 can be imaged on a display 20.

In accordance with the invention, recorded image signals from consecutive video display frames are subtracted in a subtractor 22, and only the differences in the frame images are displayed. The changes in textural pattern of the reflected ultrasonic signals can then be visualized. Static or unchanging textural patterns will be dark, whereas changing textural patterns will be bright.

Operation of the apparatus in imaging cross sections of an obstructed blood vessel is illustrated in the cross sectional views of FIGS. 2–4. FIG. 2A is a cross section of an obstructed vessel 30 including an obstruction 32, and FIG. 2B is a cross section of an unobstructed blood vessel 34.

FIGS. 3A and FIG. 3B are images of the blood vessels of FIGS. 2A and 2B, respectively, using a conventional ultrasonic body scanner and display. It will be noted that the cross sectional images of the blood vessels appear to be essentially the same since the obstruction 32 in blood vessel 30 cannot be distinguished from the blood flowing through the blood vessel since the propagation of the ultrasonic wave is essentially the same for a lesion or blood clot and for blood.

However, since the textural pattern of the obstruction 32 will remain constant whereas the textural pattern of the moving blood changes, as discussed above, the unobstructed portion of the blood vessel in FIG. 2A can be readily distinguished by determining and imaging changes in textural patterns. This is illustrated in FIG. 4A in which the unobstructed portion 38 of blood vessel 30 pulsates brightly due to changes in textural pattern whereas the portion 40 corresponding to the static obstruction remains dark. This is to be compared with the image of the unobstructed vessel 34 shown in FIG. 4B which projects a bright image for the entire vessel.

By detecting and imaging changes in textural patterns to distinguish moving ultrasonic scatterers from stationary ultrasonic scatterers, the identification and imaging of blood vessel obstructions is readily discerned. While the invention has been described with reference to a specific embodiment and application, the description is illustrative of the invention and is not to be construed as limiting the invention. Various modifications and applications may occur to those skilled in the art without departing from the true spirit and scope of the invention.

What is claimed is:

1. A method of detecting obstructions in a blood vessel comprising the steps of
   transmitting ultrasonic signals to said blood vessel,
   receiving reflected ultrasonic signals from said blood vessel,
   generating electrical signals indicative of textural patterns in response to received ultrasonic signals,
   determining changes in textural patterns represented by said electrical signals including establishing image data based on said reflected ultrasonic signals and subtracting image data for one time period from image data from another time period, and
   displaying the changes in textural patterns.

2. The method as defined by claim 1 wherein said image data comprises frame data for video display.

* * * * *